United States Patent [19]

Beachey et al.

[11] Patent Number: 5,124,153
[45] Date of Patent: Jun. 23, 1992

[54] THERAPEUTIC COMPOSITIONS AGAINST STREPTOCOCCAL INFECTIONS, TRANSFORMED HOSTS, METHODS OF IMMUNIZATION AND GENETICALLY ENGINEERED PRODUCTS

[75] Inventors: Edwin H. Beachey; Thomas P. Poirier, both of Memphis, Tenn.; Michael A. Kehoe, Durham, England

[73] Assignee: University of Tennessee Research Corp., Knoxville, Tenn.

[21] Appl. No.: 391,464

[22] Filed: Aug. 9, 1989

Related U.S. Application Data

[62] Division of Ser. No. 88,626, Aug. 24, 1987.

[51] Int. Cl.$^5$ ............ A61K 39/09; A61K 39/112
[52] U.S. Cl. ............ 424/93 P; 435/252.8; 435/253.4; 424/93 H
[58] Field of Search ............ 424/92, 93, 93 H, 93 P; 435/172.1, 252.8, 253.4, 879, 882; 530/350, 825

[56] References Cited

U.S. PATENT DOCUMENTS

| | | | |
|---|---|---|---|
| 4,404,186 | 9/1983 | Ron | 424/92 |
| 4,454,121 | 6/1984 | Beachy | 424/177 |
| 4,550,081 | 10/1985 | Stocker | . |
| 4,597,967 | 7/1986 | Beachey et al. | . |
| 4,681,762 | 7/1987 | Oeschger | 424/92 |
| 4,735,801 | 4/1988 | Stocker | . |
| 4,764,370 | 8/1988 | Fields | 424/93 |
| 4,784,948 | 11/1988 | Scott | 435/68 |
| 4,888,170 | 12/1989 | Curtiss | 424/93 |
| 4,919,930 | 4/1990 | Beachy | 424/88 |
| 4,968,619 | 4/1990 | Curtiss | 435/252.33 |

FOREIGN PATENT DOCUMENTS

| | | |
|---|---|---|
| 0060129 | 9/1982 | European Pat. Off. . |
| 8500832 | 2/1985 | PCT Int'l Appl. . |
| 8503521 | 8/1985 | PCT Int'l Appl. . |

OTHER PUBLICATIONS

*Bacterial Vaccines*, 1984. René Germanier, editor. Academic Press, New York. Chapter 5 "Typhoid Fever".
A. Brown et al., J. Infect Dis. 155(1):86–92. An attenuated aro A *salmonella typhimurium* . . .
Hogeth, S. et al., Nature 291:238–39, Aromatic dependent *S. typhimurium* are non–virulent . . .
In–Vivo Immunostimulating Activity of the 163–171 Peptide of Human Nencioni L. et al., J. Immunol 139 (3) 1987, 800–804.
Primary Prophylaxis of Rheumatic Fever State and Prospects Vaccine Inst. Hyg. Epidemiol., Prague, Czech, Ter Arkh 57 (11) 1985, 97–100.
Expression of Mycobacterium–Leprae Genes from a Streptococcus–Mutan Jacobs W R. et al., Proc. Natl. Acad. Sci. USA 83 (6) 1986, 1926–193.
In–Vivo Repackaging of Recombinant Cosmid Molecules for Analysis Salmonella–Typhimurium Strptococcus–Mutans and Mycobacerial Genom Jacobs W R., Infect. Immun., 52 (1) 1986 101–109.
Use of MuramylDipeptides in the Synthetic Vaccine Models Audibert F., Boll 1st Sieroter Milan, 64 (2). 1985. 95–102.
Molecular Analysis of DNA and Construction of Genomic Libraries of . . . Clark–Curtiss J. E. et al., J. Bacteriol 161 (3). 1985, 1093–1102.
Mono Clonal Antibodies to Streptococcal Group A Carbohydrate 2 . . . Fulton R. J. et al., J. Immunol., 131 (3). 1983. 1326–1331.
Cloning Virulence Determinants from Streptococcus Mutans and the use Hamada, Mol. Microbiol, 1986. 173–80.
Type Specific Protective Immunity Evoked by Snythetic Peptide of S. Pyogenes M.Protein (Nature, v. 292, No. 5822, Jul. 30, 1981 Beachey et al.
Expression of Protective and Cardiac Tissue Cross––Reactive Epitopes of Type 5 Streptoccal M Protein in *E. coli*, Infec. and Immun, 1985).
Cloning and Genetic Analysis of Serotype 5 M Protein Determinant of Group A Streptococci: Infec. and Immun. (1985) p. 190–197.
Cloning Virulence Determinants from S. Mutans and the use of Recombinant Clones to Construct Bivalent Oral Vaccine Strains to confer Protective Immunity against *S. Mutains*–Induced Dental Caries, (1988), Elsevia Science Publishers, p. 173–180.

*Primary Examiner*—Christine Nucker
*Assistant Examiner*—T. M. Cunningham
*Attorney, Agent, or Firm*—Weiser & Stapler

[57] ABSTRACT

Non-virulent bacteria are disclosed into which have been cloned heterologous nucleotide sequences encoded for the expression of Streptococcal M protein antigens, which are effective to elicit opsonic antibodies against Streptococcal infections. These bacteria are useful for vaccination against *Streptococcus pyogenes* bacteria.

50 Claims, No Drawings

THERAPEUTIC COMPOSITIONS AGAINST STREPTOCOCCAL INFECTIONS, TRANSFORMED HOSTS, METHODS OF IMMUNIZATION AND GENETICALLY ENGINEERED PRODUCTS

This is a division of application Ser. No. 07/088,626, filed Aug. 24, 1987.

This invention relates to immunization against Streptococcal infections, more particularly against group A streptococcal infections.

The invention has broad and important implications. As far as is known by the inventor, there is provided for the first time a biological living vehicle which carries a protective antigen of a virulent bacteria which antigen is effective to immunize against infections caused by the virulent bacteria. It is contemplated that the embodiments here disclosed are applicable to broader and more far reaching applications, methods and uses.

The search for a safe and effective vaccine against those strains of group A streptococci that trigger rheumatic fever and rheumatic heart disease has been ongoing for more than sixty years. Lancefield, "Current Knowledge of Type-Specific M Protein Antigens to Group A Streptococci," *J. Immunol,* Vol. 89, pp. 307–313 (1962). It has been reported that few bacterial species have been subjected to more intensive investigation during the century than *Streptococcus pyogenes* or the group A streptococcus. As conviction grew that this organism was first the principal, and then the exclusive agent for acute rheumatic fever, researchers sought with much determination and effort to dissect out the product of the bacterium whose toxic or antigenic components might touch off the rheumatic process. For a thorough study of rheumatic fever and streptococcal infection See Stollerman, *Rheumatic Fever and Streptococcal Infection* (New York Clinical Cardiological Monographs, Grune and Stratton, 1975). The central role of M protein in immunity against group A streptococci has been reviewed by Stollerman. Reference is also made to Beachey and Seyer, "Primary Structure and Immunochemistry of Group A Streptococcal M Proteins," Seminars in Infectious Disease, Vol.4, pp. 401–410 (J. B. Robbins, J. C. Hill and J. C. Sadoff, eds., Georg Thiemeverlag, pub., New York and Stuttgart, 1982).

Most efforts to develop a vaccine were frustrated by severe toxic reactions to almost any Streptococcal product introduced into the human host. Some of these products have been shown to give rise to antibodies that cross react with host tissues, especially the heart. Kaplan and Meyerserian, "An Immunological Cross-Reaction Between Group A Streptococcal Cells and Human Heart Tissue," *Lancet,* Vol. i, pp. 706–710 (1962); Zabriskie and Freimer, "An Immunological Relationship Between the Group A Streptococcus and Mammalian Muscle," *J. Exp. Med,* Vol. 124, pp. 661–678 (1966). Although it has been long established that the M protein on the surface of group A Streptococcus contains the protective antigens of these organisms, the fear has been that the isolated M protein may be associated with potentially harmful tissue cross-reactive antigens that give rise to rather than prevent, rheumatic fever. This fear has been perpetuated by the finding that certain rheumatogenic Streptococci produce M proteins that are closely associated with a heart cross-reactive antigen. Kaplan, "Immunologic Relation of Streptococcal and Tissue Antigen. I. Properties of an Antigen in Certain Strains of Group A Streptococci Exhibiting an Immunologic Cross-Reaction with Human Heart Tissue," *J. Immunol.* Vol. 90, p. 595 (1963). Indeed, recently it has been established that one of the M protein molecules contains, within its covalent structure, an epitope that elicits a protective anti-Streptococcal antibody that also cross-reacts with a sarcolemmal protein of human heart tissue. Dale and Beachey, "Protective Antigenic Determinant of Streptococcal M Protein Shared with Sarcolemmal Membrane Protein of Human Heart," *J. Exp. Med.,* Vol. 156, pp. 1165–1176 (1982).

U.S. Pat. No. 4,284,537, to E. Beachey, issued Aug. 18, 1981, disclosed the amino acid sequence of two peptide fragments derived from type 24 M protein. It also disclosed that each of these natural fragments, when covalently linked to a carrier such as a polylysine, was able to elicit type-specific opsonic antibodies effective against *Streptococcus pyogenes.* Each of these fragments was a natural extract, and each contained 35 amino acids.

U.S. Pat. No. 4,454,121, to E. Beachey, issued Jun. 12, 1984, disclosed a synthetic peptide (S-CB7) and that one of the protective determinants is located in a specific fragment of S-CB7 of type 24 M protein which contains only twelve amino acid residues (S-CB7(18-29)). S-CB7, as described, differs from the native CB-7 fragment in that the COOH-terminal residue of S-CB7 is methionine, in contrast to homoserine. The specification also teaches and described covalently linked conjugates of S-CB7 and appropriate hapten carriers, natural, like BSA or OVA or synthetic, like polylysine. Further details about this work have been published in *Nature* on Jul. 30, 1981, by Beachey et al, 292, pages 457–459.

U.S. Pat. No. 4,521,334, entitled "Synthetic Polypeptide Fragments," to Edwin H. Beachey, issued Jun. 4, 1985, discloses the amino acid sequence of three peptide fragments CB3, CB4, and CB5, and 35 and 37 amino acid sequences of type 24 M which contain antigenic determinants corresponding to the antigenic determinants contained in CB3–CB7. U.S. Pat. No. 4,597,967 entitled "Synthetic Polypeptide Fragments," to Edwin H. Beachey, issued Jul. 1, 1986, discloses that these fragments, when covalently linked to a carrier such as polylysine, are able to elicit type-specific opsonic antibodies effective against *Streptococcus pyogenes.*

U.S. application Ser. No. 739,963 entitled "Biologically Active Hybrid Peptides of Streptococcal M Protein and Compositions and use" to Edwin H. Beachey et al filed May 31, 1985 disclosed peptide sequences containing fragments of M5, M6, and M24 proteins which are able to elicit opsonic and bactericidal antibodies to *Streptococcus pyogenes* which are not serologically cross-reactive with tissue antigens of the human or host heart. U.S. application Ser. No. 839,750 entitled "Synthetic M Proteins-Streptococci Type 6" to Edwin H. Beachey, et al filed Mar. 14, 1986 discloses the synthesis of type M6 protein antigen conjugates. U.S. application Ser. No. 858,436 entitled "Localization of Protective Epitopes of the Amino Terminus of Type S Streptococcal M Protein," to Edwin H. Beachey, et al filed May 1, 1986 disclosed the synthesis of Type M5 protein antigen conjugates.

The above patents disclose small peptide fragments which are immunogenic and contribute to the development of a safe and effective vaccine against those streptococcal infections that initiate fevers and rheumatic heart disease. The approach was that very small peptides would permit disposal of a large portion of the M protein molecule and therefore, should reduce the chances of eliciting immunological cross-reactions against host tissues. See for instance the above-referred to U.S. Pat. No. 4,454,121 Columns 1 and 2.

For additional information regarding type specific protective immunity evoked by synthetic peptides of *Streptococcus pyogenes* M protein, See, Beachey, et al., "Type Specific Protective Immunity Evoked by Synthetic Peptide of *Streptococcus pyogenes* M Protein," *Nature*, Vol. 292, No. 5822, pp 457–459 (Jul. 30, 1981).

For additional literature in this field See Hasty, et als, "Hybridomas Antibodies Against Protective and Non-Protective Antigenic Determinants of a Structurally Defined Polypeptide Fragment of Streptococcal M Protein," *J. Exp. Med.* Vol. 155, p 1010 (April 1982); and Hopp and Woods, "Prediction of Protein Antigenic Determinants from Amino Acid Sequences," *Proc. Natl. Acad. Aci. USA*, Vol. 78, No. 6, pp. 3824–3828 (June 1981).

Notwithstanding these advances, there remains a serious need, as yet unfilled for an orally administrable vaccine incorporating these non-cross-reactive immunogenic polypeptides. By administering these peptides in the form of an attenuated non-virulent recombinant bacterium capable of their synthesis, the present invention marks another forward step and provides another advance in the medical sciences, particularly in the control of Streptococcal infections.

Numerous serotypes of M proteins are known, coded on genes that are alleles of each other. Each serotype corresponds to a different strain of *S. pyogenes*, and these serotypes differ only by their amino terminal sequences.

The present invention relates in a general way to a genetic engineering approach to the synthesis of a Streptococcal M protein antigen or antigen fragment which is effective to elicit opsonic antibodies against Streptococcal infections.

In a more specific sense the invention provides a transformed non-virulent bacterium which contains a heterologous nucleotide sequence which nucleotide sequence is encoded for and expresses a Streptococcal M protein antigen.

The invention also provides a transformed non-virulent host in which the expressed Streptococcal M protein antigen is effective to elicit opsonic antibodies against streptococcal infection.

Another object of the invention is to also provide a protein antigen which is effective against virulent forms of the non-virulent bacterium.

A specific object of the invention is to provide a transformed non-virulent bacteria of the genus Salmonella, specifically the *typhimurium* species, which carries a plasmid which encodes an M protein gene, more specifically the type 5 M protein gene.

Another object of the invention is to provide a Streptococcal M protein antigen which is effective to elicit opsonic antibodies that confer specific immunity against streptococcal infections.

An object of this invention is to provide a multivalent Streptococcal M protein antigen which is effective to elicit opsonic antibodies against more than one serotype M Streptococcal strain.

Another object of the invention is to provide an expressed Streptococcal M protein antigen which is expressed in the cytoplasm and not expressed on the surface of the bacterium.

It is a further object of the invention to provide a Streptococcal M protein antigen which when expressed by the host, particularly a non-virulent heterologous microbial host into which the gene for the Streptococcal M protein antigen has been cloned, is an effective antigen which elicits immunity and is not serologically cross-reactive with human tissue antigens, especially those for the heart. A further object of the invention is a transformed non-virulent bacterium which is of the non-group A species of the genus Streptococcus.

Another object of this invention is a transformed host, e.g., a bacterium, particularly a non-virulent enteric bacterium, which, despite its non-virulence, will still elicit antibodies. It is an object of this invention to provide a transformed non-virulent host bacterium that will not colonize in the subject to be immunized, but will multiply to the limited extent necessary to elicit the antibodies.

An object of this invention is the transformation of *Salmonella typhimurium*. Another object of this invention is the transformation of *Streptococcus sanguis*.

Another object of the invention is a transformed non-virulent host bacterium into which a heterologous nucleotide sequence of another bacterial species has been cloned, which nucleotide sequence is encoded for and expresses the protein antigen which is effective to elicit opsonic antibodies against the other bacterial species.

Another important object of the invention is to provide the nucleotide sequences carried by the gene which codes for and expresses the antigens of the other bacterial species.

Another object of the invention is to provide various other genetically engineered components leading to the transformed non-virulent host.

Another object of the invention is to clone into the host bacterium, the nucleotide sequences encoded for immunogenic polypeptides effective to elicit opsonic antibodies against Streptococcal infections, in particular for Streptococcal serotypes 5, 6 and 24.

Another object of the invention is to clone into the host bacterium, the nucleotide sequences encoded for an *E. coli* surface antigen that elicits anti-adhesive antibodies.

Another object of the invention is the genetic engineering steps which leads to the preparation of the non-virulent bacteria.

Another object of the invention is the manufacture of plasmids and object constructs necessary to clone into the *S. typhimurium* strain the heterologous nucleotide sequence that expresses the desired Streptococcal M protein antigens. An important object of the invention is the manufacture of plasmids that are stably expressed in Aro−*S. typhimurium* SL3261.

Another object of the invention is a method of immunization of a mammal such as a human in which there is administered to that mammal is a dosage effective to elicit opsonic antibodies and confer systemic immunity against streptococcal infections, the transformed non-virulent bacterium described above containing the heterologous nucleotide sequence. Plasmids (and vectors) are also objects of the invention.

An important object of the invention is the oral administration of the composition of this invention, although other administrations are also provided by this invention including by parental route.

An important aspect of the invention is to provide immunity against oral infections of the streptococcal type.

Another aspect of the invention is to provide a non-virulent composition which is very well tolerated by the subject to which the composition is administered.

It is a noteworthy aspect of the invention that the immunity to the patient is systemic and is conferred comparatively rapidly and completely even when administered orally.

Other objects of the invention will become apparent from the description which follows. Other features and advantages of the invention will appear from the examples which follow and by referring to the appended drawing in which:

FIG. 1 shows Immunoblot analysis of type 5M protein expressed by pMK 207-transformed *Salmonella typhimurium* LB5000 (Lane 1) and SL3261 (Lane 2-9).

In addition to the patents and other publications mentioned above, other prior art which has been taken into consideration in the description of this invention includes:

Beachey, et als., "Repeating Covalent Structure and Protective Immunogenicity of Native and Synthetic Polypeptide Fragments of Type 24 Streptococcal M Protein," *J. Biol. Chem,* Vol. 258, No. 21 pp 13,250–13,257 (1983).

van de Rijn, et als., "Group A Streptococcal Antigens Cross-Reactive with Myocardium," *J. Exp. Med.,* Vol. 146, pp. 579–599 (1977).

van de Rijn, et als., "Immunochemical Analysis of Intact M Protein Secretd From Cell Wall-Less Streptococci," *Infect. Immun.,* Vol. 32, pp. 86–91 (1981).

Edman and Begg, "A Protein Sequenator," *European J. Biochem.* Vol. 1, pp. 80–91 (1967).

Phillips, et als., "Streptococcal M Protein: Helical Coiled - Coil Structure and Arrangement on the Cell Surface," *Proc. Natl. Acad. Sci. USA,* Vol. 78, No. 8 pp. 4689–4693 (August 1981).

Laver, et als., ∂Antigenic Drift in Type A Influenza Virus: Peptide Mapping and Antigenic Analysis of A/PR/8/34(HON1) Variants Selected With Monoclonal Antibodies," *Proc. Natl. Acad. Sci. USA,* Vol. 76, No. 3, pp. 1425–1429 (March 1979).

Atassi, "Antigenic Structure of Myoglobin: The Complete Immunochemical Anatomy of a Protein and Conclusions Relating to Antigenic Structures of Proteins," *Immunochemistry,* Vol. 12, pp. 423–438 (1975).

Kabat, *Structural Concepts in Immunology and Immunochemistry,* pp. 89–100 (Holt, Rhinehart & Winston, New York, (1968).

Nisonoff, *Methods in Immunology and Immunochemistry,* Vol. 1, pp. 120–187 (1977).

Munoz, *Methods in Immunology and Immunochemistry,* Vol. 3, pp. 146–160 (1970).

Manjula and Fischetti, "Tropomyosin-like Seven Residue Periodicity in Three Immunologically Distinct Streptococcal M Proteins and its Implications for the Antiphagocytic Property of the Molecule," *J. Exp. Med.,* Vol. 155, pp. 695–708 (1980).

Beachey and Stollerman, "Toxic Effects of Streptococcal M Protein on Platelets and Polymorphonuclear Leukocytes in Human Blood," *J. Exp. Med.,* Vol. 134, pp. 351–365 (1971).

Dale, et als., "Heterogenecity of Type-Specific and Cross-Reactive Antigenic Determinants Within a Single M Protein of Group A Streptococci," *J. Exp. Med.,* Vol. 155, pp. 1026–1038 (1980).

Beachey, et als. "Purification and Properties of M Protein Extracted from Group A Streptococci with Pepsin: Covalent Structure of the Amino Terminal Region of Type 24 M Antigen," *J. Exp. Med.* Vol. 145 pp. 1469–1483 (1977).

Beachey, et als., "Primary Structure of Protective Antigens of Type 24 Streptococcal M Protein," *J. Biol. Chem.,* Vol. 255, pp. 6284–6289 (1980).

Beachey, et als., "Repeating Covalent Structure of Streptococcal M Protein," *Proc. Natl. Acad. Sci. USA,* Vol. 75, pp. 3163–3167 (1978).

Beachey, et als., "Human Immune Response to Immunization with a Structurally Defined Polypeptide Fragment of Streptococcal M Protein," *J. Exp. Med.,* Vol. 150, pp. 862 (1979).

Brown, et al., "An Attenuated aroA *Salmonella typhimurium* Vaccine Elicits Humoral and Cellular Immunity to Cloned -Galactosidase in Mice," *The Journal of Infectious Diseases,* Vol. 155, No. 1 (January 1987). This publication discusses *Salmonella typhimurium* strain SL3261, and an attenuated aroA vaccine strain, which was used as a carrier for the plasmid pXY411.

This publication of Brown, et al., is incorporated herein by reference. Another publication of interest is Hoiseth and Stocker, "Aromatic-dependent *Salmonella typhimurium* are Non-Virulent and Effective as Live Vaccines," *Nature,* Vol. 291 (May 21, 1981); Smith, et al., "Aromatic-Dependent *Salmonella typhimurium* are Non-Virulent and Effective as Live Vaccines," *Am. J. Vet. Res,* Vol. 45, No. 1 (January 1984); Smith et al., "Vaccination of Calves Against Salmonella Dublin with Aromatic-Dependent *Salmonella typhimurium,*" *Am. J. Vet. Res.,* Vol. 15, No. 11 (November 1984); Maskell, et al., "Attenuated *Salmonella typhimurium* as Live Oral Vaccines and Carriers for Delivering Antigens to the Secretory Immune System," *Vaccines 86* (Cold Spring Habor Laboratory 1986).

Patents in the genetic engineering field which are of general interest include:

U.S. Pat. No. 4,428,941 entitled "Nucleotide Sequence Coding the Surface of the Hepatitis B Virus, Vector Containing Said Nucleotide Sequence, Process Allowing the Obtention Thereof and Antigen Obtained Thereby," issued to Francis Galibert, et als., on Jan. 31, 1984; U.S. Pat. No. 4,518,584 entitled "Human Recombinant Interleukin-2 Muteins," issued to Mark, et als., on May 21, 1985; U.S. Pat. No. 4,588,585 entitled "Human Recombinant Cysteine Depleted Interferon-B Muteins," issued to Mark et als., on May 13, 1986; and U.S. Pat. No. 4,625,252 entitled "Recombinant Bacterial Plasmids Containing the Coding Sequences of Insulin Genes," issued to Rutter, et als., on Mar. 24, 1987.

U.S. Pat. No. 4,666,846 entitled "Novel Cloning Vectors Containing Selectable Genetic Markers for Use in Streptomyces and Related Organisms," issued to Fayerman, et als. on May 19, 1987; and U.S. Pat. No. 4,666,847 entitled "Recombinant DNA Means and Methods," issued to Alford, et als., on May 19, 1987.

In accordance with the invention it is preferable that the plasmid which encodes the M protein gene be cloned first and expressed in *Escherichia coli.* Any other enteric bacilli of the coliform group such as Klebsiella or Enterobacter can be used, but normally *E. coli* is preferred. Therefore the plasmid carrying the M gene is isolated and purified and then a construct is built to transform the desired non-virulent bacteria, such as the aroA—*S. typhimurium* (SL3261). It is to be noted that this mutant strain exhibits a nutritional marker both for PABA and 2,3-DHB. See Brown et al., cited above. It is to be noted that another desired specie of *S. typhimurium* is recA⁻ *S. typhimurium*, particularly strain Ty21a. See Clements, et al., "Construction of a Potential Live Aro Vaccine for typhoid type fever and cholorea—*E. coli*—related diarrheas," *Infect. Immun.*, 46:564-9 (1984). Also see the other references cited in the above cited Brown, et al., article, which are also incorporated herein by reference.

It is preferred to obtain the M protein gene from a virulent strain of *S. pyogenes*. However, it is possible to obtain the gene from an attenuated, non-virulent strain of *S. pyogenes*, or even to fabricate the nucleotide sequence coded for the desired M protein.

The recombinant DNA cloning vectors of the present invention are not limited for use in a single species or strain of Salmonella. To the contrary, the vectors are broadly applicable and can be transformed in host cells of other gram negative bacteria such as of the Enterobacteriaceae genus (such as Shigella and Klebsiella like (*Klebsiella penumoniae,* Enterobacter like *Enterobacter aerogenes*). Salmonellae, such as *Salmonella arizona,* and Citrobacter may be used if appropriately rendered non-virulent or attenuated.

Common Salmonella species which may be used when attenuated and rendered non-virulent include the following: *S. paratyphi A, S. schottmulleri, S. typhimurium, S. paratyphi C, S. choleraesuis, S. montevideo, S. newport, S. typhi, S. enteritidis, S. gallinarum, S. anatum.*

In accordance with the invention there may also be used as host for the recombinant DNA cloning vectors of the present invention bacteria of the Streptococcus genus which are non-virulent or which have been made non-virulent or attenuated, including Streptococci of the immunological groups A-O but generally other than A. Suitable Streptococci which can be used as bacterial host include *S. cremoris, S. faecalis, S. salivarius, S. mitior, S. mitis, S. mutans* and *S. sanguis,* the latter species is presently a preferred specie.

Additional appropriate microorganisms which may be attenuated and transformed in accordance with the invention are known. Reference may be made to Davis, et al., *Microbiology,* (Harper & Row, Second edition, 1973).

Generally any enteric bacterium may serve as the host bacterium. It is preferable that the host bacterium only survive in the subject long enough to elicit the opsonic response, but generally any bacterial strain that has been attenuated not to colonize but will still multiply to a limited degree to elicit antibodies to the foreign protein can be used. In a preferred embodiment of the invention the Aro$^-$ strain of *S. typhimurium* is used, which requires two metabolites not found in mammalian tissues, PABA and 2,3-DHB. As a result, the innoculated bacteria die after several generations from lack of these metabolites. See Hoiseth and Stocker, cited above.

However, any mutated microbial agent with a metabolic deficiency for nutritional compounds not found in the tissues of the subject to be immunized, or one so made by genetic manipulations, may be employed.

It is to be noted that the non-virulent aro$^-$*Salmonella typhimurium* SL3261 into which a plasmid containing the structural gene encoding the serotype 5M protein antigen has been transformed expresses the entire M 5 protein molecule, which expression is confined almost exclusively to the *S. typhimurium* cytoplasmic compartment. It is a unique and unexpected aspect of this invention that an immunogenic and protective surface antigen such as the Streptococcal M protein antigen is expressed in the cytoplasm of the non-virulent host bacterium.

Thus it can be seen that in accordance with the invention the desired nucleotide sequence which codes for and expresses the protein antigen which is effective to elicit opsonic antibodies against streptococcal infections particularly of the serotype 5, can be cloned into a variety of hosts. In a broader sense therefore the transformed host in which the nucleotide sequence is found after replication need not be heterologous with respect to the nucleotide sequence, nor does the sequence need to be heterologous with respect to the microorganisms.

In accordance with a specific embodiment of the method of immunization of a warm-blooded animal, it has been showed that a) peroral administration of up to $1.65\times10^9$ mutant non-virulent Salmonella containing the plasmid pMK207 encoding serotype 5 Streptococcal M protein was well tolerated in mice; b) plasmid mPK207 was extremely stable both in vitro and in vivo; c) the mice receiving the highest dose ($10^9$) of bacteria harbored the microorganisms in the liver for as long as three weeks without ill effects; d) the mice immunized orally with non-virulent transformed Salmonella expressing the serotype 5 Streptococcal M protein antigen gene developed opsonic serum antibodies as early as three weeks against serotype M5 Streptococci; and e) the immunized mice were completely protected at three weeks against intra-peritoneal challenges of the homologous serotype M5 (but not the heterologous serotype M24) Streptococci. It is noteworthy that no cross-reactive immunity is observed when the composition of the invention is administered orally. The cytoplasmic expression of the M protein antigen in the non-virulent bacterium is especially advantageous for this oral administration. The antigen is protected within the cytoplasm of the non-virulent bacterium from the acids of the stomach and other damaging agents until the non-virulent cell dies and releases the antigen, ordinarily in the small intestine, the preferred location for delivery of the antigens.

In accordance with the invention the non-virulent bacterium may also be used as a host for recombinant DNA cloning vectors containing nucleotide sequences which code for and express immunogenic polypeptides which are specifically effective to confer immunity against Streptococcal infections and which are not cross-reactive with human tissue antigens, especially those of the heart.

Immunogenic polypeptides in accordance with the invention include synthetic oligopeptides copying regions of M protein molecules lacking auto-immune epitopes, as described in U.S. Pat. No. 4,284,537 issued to E. Beachey on Aug. 18, 1981, U.S. Pat. No. 4,454,121 issued to E. Beachey on Jun. 12, 1984, U.S. Pat. No. 4,521,334 issued to E. Beachey on Jun. 4, 1985, U.S. Pat. No. 4,597,967 issued to E. Beachey on Jul. 1, 1986, U.S. application Ser. No. 739,963, on E. Beachey, et al, filed May 31, 1985, U.S. application Ser. No. 839,750 to E. Beachey et al filed Mar. 14, 1986 and U.S. application Ser. No. 858,436 to E. Beachey, et al filed May 1, 1986, all cited above and incorporated by reference.

The capacity of serotype M 24 polypeptides as a carrier for a highly multi-valent vaccine is being tested with other serotype M polypeptide fragments.

Another approach of the invention has been to use *Streptococcus sanguis* bacteria which have been transformed with the M protein - expressing plasmids. The expression of serotype type 5 M protein in *S. sanguis* has been accomplished. The M protein gene was carried on a shuttle vector plasmid and transformed into the host bacterium, which was shown to express serotype 5 M protein fibrils on the surface of the organism. Moreover, the organism were able to bind fibrinogen which in turn rendered the microorganism resistant to phagocytosis.

In accordance with the invention a desirable method for immunizing against Streptococcal infections is to instill attenuated *S. sanguis*, intranasally to evoke local immune responses at the very site where Streptococci commonly enter the host.

Another approach of the invention has been to clone into the host organism, together with the M protein - expressing plasmid, a plasmid expressing the antigen of a third bacterial species. In particular, a pSH-2 plasmid cloned from the CSH50 strain of *E. coli* has been cloned into *Sal. typhimurium* causing the host to express an *E. coli* 29 kilodalton surface antigen that elicits Fim H antiadhesive antibodies. These antiadhesive antibodies are not only effective against *E. coli*, they are also effective against other gram negative bacteria.

Other advantages characteristic of the invention will appear from the non-limiting examples which follow.

EXAMPLE 1

TRANSFORMATION OF NON-VIRULENT HOST BACTERIUM TO EXPRESS STREPTOCOCCAL M PROTEIN

The aro$^-$ strain of *Salmonella typhimurium* SL3261, developed by Stocker and Hoseith (cited above) was chosen because this mutant form of microbial agent is capable of invasion but not causing disease. This mutant strain exhibits a nutritional marker for both p-aminobenzoic acid (PABA) and 2,3-dihydrobenzoic acid (DHB). See Stocker and Hoseith, cited above.

The M5 protein antigen structural gene (smp 5) was cloned and expressed in *E. coli* LE392 as described by Kehoe, et als., "Cloning and Genetic Analysis of Serotype 5M Protein Determinant of Group A Streptococci: Evidence for Multiple Copies of the M5 Determinant in the *Streptococcus pyogenes* Genome," *Infect Immun.*, Vol. 48, pp 190–197 (1985) and Poirer, et als., "Expression of Protective and Cardiac Tissue Cross-Reactive Epitopes of Type 5 Streptococcal M Protein in *Escherichia coli*," *Infect. Immun.* Vol. 48, pp. 198–203 (1985), both of which are incorporated herein by reference.

The plasmid pMK207 was isolated, purified, and transformed first into an rm+ strain LB5000 of *Sal. typhimurium*, as described by Bullas nd Ryo, "*Salmonella typhimurium* LT2 Strains which are r−m+ for all Three Chromosomally Located Systems of DNA Restriction and Modification," *J. Bacteriol*, Vol. 156, pp. 471–474 (1983) and Lederberg and Cohen, "Transformation of *Salmonella typhimurium* by Plasmid Deoxyribonucleic Acid," *J. Bacteriol.*, Vol. 119, pp. 1072–1074 (1974), both of which are incorporated herein by reference. The plasmid isolated and purified from LB5000 was then used to transform the aro$^-$*Sal. typimurium* SL3261 in using the same above-cited procedures described by Lederberg and Cohen and Bullas and Ryo.

The transformed LB5000 and SL3261 expressed the entire M5 protein molecule as demonstrated by Western blot analysis of whole cell lysates (FIG. 1; lanes 1 and 2). The typical triplet of M5 protein (See Poirer, et als., and Kehoe, et als, cited above) migrated as bands of $M_r$ 59, 56 and 54k. Preliminary studies designed to determine the location of the M5 protein as expressed by *Sal. typhimurium* SL3261 indicated that the recombinant protein was confined almost exclusively to the cytoplasmic compartment. The M5 protein was expressed in a stable fashion by SL3261 even in the absence of antibiotic pressure, i.e., expression was apparent following repeated subscultures over five days, which represents approximately 35 generations of growth (FIG. 1; lanes 3–8).

EXAMPLE 2

MOUSE TOLERANCE OF TRANSFORMED *SAL. TYPHIMURIUM* SL3261

In preliminary studies, BALB/c mice were challenged with increasing doses of SL3261–pMK207 to determine whether or not the animals would tolerate the transformed organisms. None of the mice receiving up to a maximum of $1.65\times10^9$ organisms per oral dose either sickened or died. At 1, 3, 5 and 10 weeks after innoculation, two mice from each dosage group were sacrificed and their livers, spleens and intestines cultured for SL3261–pMK207 on McConkey's agar containing 50 mg/ml kanamycin sulfate and 10 mg/ml each of PABA and DHB. Non-lactose fermenting colonies could be isolated at one week only from the mice receiving $10^6$ organisms or more, and at three weeks, only from those receiving $10^9$ organisms (Table 1). No isolates were recovered after three weeks. The colonies isolated at three weeks expressed an intact M5 protein, which suggests that smp5 was stable in vivo (FIG. 1; lane 9). The 1, 3, 5, 9, 10, 15 and 20 weeks sera from mice innoculated orally were shown to exhibit antibodies against type 5M protein and type 5 Streptococci by ELSIA and opsonization experiments, respectively (Table 2). The saliva obtained from mice that were 20 weeks post-immunization was also shown to possess anti-M5 protein antibodies, primarily of the IgA class (Table 3).

TABLE 1

DISTRIBUTION OF *SALMONELLA TYPHIMURIUM* SL3261 IN THE ORGANS OF BALB/c MICE AFTER ORAL IMMUNIZATION

| INOCULATION DOSE[1] | | SALMONELLA DISTRIBUTION IN ORGANS[2]: INTESTINE | | | LIVER - GALL BLADDER | | | SPLEEN | | |
|---|---|---|---|---|---|---|---|---|---|---|
| Initial | Boost | Week 1 | Week 2 | Week 3 | Week 1 | Week 2 | Week 3 | Week 1 | Week 2 | Week 3 |
| $1.7\times10^9$ | $1.1\times10^9$ | $2.1\times10^4$ | <50 | <50 | $4\times10^2$ | $3\times10^2$ | <50 | $4\times10^2$ | <50 | <50 |
| $1.7\times10^8$ | $1.1\times10^8$ | <200 | <50 | ND[3] | $8\times10^2$ | <50 | ND | $4\times10^2$ | <50 | ND |
| $1.7\times10^7$ | $1.1\times10^7$ | <200 | <50 | ND | $1\times10^2$ | <50 | ND | $1\times10^2$ | <50 | ND |
| $1.7\times10^6$ | $1.1\times10^6$ | <100 | ND | ND | <50 | ND | ND | <50 | ND | ND |
| $1.7\times10^5$ | $1.1\times10^5$ | <100 | ND | ND | <50 | ND | ND | <50 | ND | ND |

TABLE 1-continued DISTRIBUTION OF *SALMONELLA TYPHIMURIUM* SL3261 IN
THE ORGANS OF BALB/c MICE AFTER ORAL IMMUNIZATION

| INOCULATION DOSE[1] | | SALMONELLA DISTRIBUTION IN ORGANS[2]: | | | | | | | |
|---|---|---|---|---|---|---|---|---|---|
| | | INTESTINE | | | LIVER - GALL BLADDER | | | SPLEEN | | |
| Initial | Boost | Week 1 | Week 2 | Week 3 | Week 1 | Week 2 | Week 3 | Week 1 | Week 2 | Week 3 |
| $1.7 \times 10^4$ | $1.1 \times 10^4$ | <100 | ND | ND | <50 | ND | ND | <50 | ND | ND |

[1]Mice were given serially 10-fold diluted oral doses of *S. typhimurium* strain SL3261 beginning with $1.7 \times 10^9$ colony forming units (cfu) on day 1 (initial dose), with an oral booster dose beginning with $1.1 \times 10^9$ cfu on day 5. Each dose was suspended in 25 μl of phosphate buffered saline (PBS, pH 7.2) containing 5 μg ml$^{-1}$ kanamycin sulfate, and 1 μg ml$^{-1}$ each of paraminobenzoic acid (PABA) and 2,3-dihydroxybenzoic acid (DHB). Mice were sacrificed at 1, 2, and 3 weeks after administration of the initial dose.
[2]Intestine (pyloric sphincter to rectum), liver-gall bladder, and spleen were removed aseptically, placed in PBS, homogenized with a Cellector TM (100 mesh; Bellco), and plated onto MacConkey agar containing 10 μg ml$^{-1}$ each of PABA and DHB with or without 50 μg ml$^{-1}$ of kanamycin.
[3]Not determined.

TABLE 2

Opsonization of M Type 5 *S. pyogenes* with Mouse Anti-M5-Protein-Serum Obtained from BALB/c Mice Orally Immunized with *S. typhimurium* SL3261-pMK207 and their Anti-pepM Protein ELISA Titers.

| | ELISA Titer[1] | | | Percent Opsonization[2] | |
|---|---|---|---|---|---|
| Test Serum | IgA | IgG | IgM | Type 5 | Type 24 |
| Pre-Immune | <50 | <50 | <50 | 0 | 2 |
| 1 week | 100 | 200 | <50 | 4 | 4 |
| 3 weeks | 400 | 400 | <50 | 36 | 0 |
| 5 weeks | 800 | 800 | <50 | 52 | 2 |
| 9 weeks | 100 | 1600 | 200 | 90 | 2 |
| 10 weeks | 50 | 800 | 400 | 92 | 2 |
| 15 weeks | 100 | 800 | 400 | 52 | 0 |
| 15 weeks[3] | 800 | 12800 | 800 | 82 | 0 |
| 20 weeks | <50 | 400 | 200 | 10 | 2 |
| 20 weeks[3] | 400 | 3200 | 200 | 80 | 2 |
| Anti-pepM5[4] | ND[5] | ND | ND | 96 | 2 |
| Anti-pepM24[4] | ND | ND | ND | 0 | 98 |

[1]ELISA titers were determined using immobilized pepM5 reacted with BALB/c mouse anti-SL3261-pMK207-sera followed with peroxidase conjugated goat anti-mouse -IgA, -IgG, or -IgM. All mouse antisera reacted against immobilized pepM24 gave titers of <50.
[2]Opsonization was determined as the percent of total neutrophils with associated streptococci.
[3]Mice were boosted 48 hours prior to bleed out with 50 μg of pepM5 in 0.1 ml of phosphate buffered saline, pH 7.2.
[4]Both anti-pepM5 and anti-pepM24 were prepared in rabbits to serve as positive (homologous reaction) and negative (heterologous reaction) controls.
[5]The antibody titers for the rabbit anti-pepM5 or anti-pepM24 were not determined.

TABLE 3

Salivary Antibody Response[1] Against M5-Protein in BALB/c Mice Immunized Orally with *S. typhimurium* SL3261-pMK207.

| | ELISA Titer[2] Against pepM5 | |
|---|---|---|
| Test Serum | IgA | IgA + IgG + IgM |
| Pre-Immune | <4 | <4 |
| 20 Weeks[3] | 32 | 32 |
| 20 Weeks + Boost[4] | 64 | 128 |

[1]Saliva was collected and peeled from mice (four per group) following induction intraperitoneally with 0.1 ml of 2% pilocarpine.
[2]ELISA titers were determined using immobilized pepM5 reacted with saliva (serially diluted two-fold) collected from BALB/c mice immunized with SL3261-pMK207 followed with peroxidase conjugated goat anti-mouse -IgA or anti-mouse -IgA + IgG + IgM mixture.
[3]Mice were immunized 20 weeks prior to the saliva collection (see Table 2).
[4]Mice were injected with a booster dose of 50 μg of pepM5 in 0.1 ml of phosphate buffered saline, pH 7.2, 60 hours prior to saliva collection.

EXAMPLE 3

A group of mice was innoculated orally with two doses of SL3261-pMK207 and challenged 22 days after the first dose with type 5 or 24 Streptococci, or the virulent parent *Sal. typhimurium* 1344 (Table 3). As can readily be seen by the results, the mice receiving the M5 expressing *Sal. typhimurium* mutant were completely protected against an intra-peritoneal challenge of type 5 Streptococci, but not with type 24 Streptococci. Control mice challenged intra-peritoneally with the virulent SL1344 *Sal. typhimurium* were also protected. The type 5 challenged mice were protected against a dose that exceeded the LD$_{50}$ by 100-fold (Table 4). This protection against parenteral challenge by type 5 Streptococci indicates that the immunity conferred is systemic.

TABLE 4

Challenge by Intra-Peritoneal Injection of M Type 5 and Type 24 Streptococci or *S. typhimurium* SL1344 in BALB/c Mice Immunized Orally[1] with Live aro$^-$ *S. typhimurium* Transformed with pMK207 Expressing Type 5 M Protein.

| Challenge Organisms[2] | Dose[3] | Survival[4,5] | |
|---|---|---|---|
| | | Unimmunized | Immunized |
| M5 Streptococci (Smith strain) | $1.7 \times 10^4$ | 2/4 | 4/5 |
| | $1.7 \times 10^5$ | 0/4 | 5/5 |
| | $1.7 \times 10^6$ | 0/4 | 5/5 |
| M24 Streptococci (Vaughn strain) | $1.6 \times 10^3$ | 1/3 | 1/3 |
| | $1.6 \times 10^4$ | 0/3 | 0/3 |
| | $1.6 \times 10^5$ | 0/3 | 0/3 |
| *S. typhimurium* (Strain SL1344) | $7.3 \times 10^1$ | 0/3 | 3/3 |
| | $7.3 \times 10^2$ | 0/3 | 3/3 |
| | $7.3 \times 10^3$ | 0/3 | 3/3 |

[1]Each immunized mouse received $1.2 \times 10^9$ pMK207-transformed SL3261 *S. typhimurium* colony forming units (cfu) at 22 days and $1.6 \times 10^9$ cfu at 17 days before challenged. Each dose was administered orally suspended in 25 μl of phosphate buffered saline containing 5 μg ml$^{-1}$ kanamycin sulfate, and 1 μg ml$^{-1}$ each of paraminobenzoic acid and 2,3-dihydroxybenzoic acid.
[2]The LD$_{50}$ for M5 and M24 streptocci, and SL1344 in BALB/c mice was approximately $2 \times 10^4$, $3 \times 10^3$, and $1 \times 10^0$ CFU, respectively.
[3]Dose was determined as the CFU administered.
[4]Survival was recorded as the number of surviving mice divided by the number of mice challenged.
[5]All recorded deaths occurred between 3 and 6 days after challenge. All surviving mice appeared healthy up to 30 days after challenge.

A group of BALB/c mice which had been immunized orally with SL3261-pMK207 were challenged intra-nasally with type 5 or 24 Streptococci, or the virulent parent *Sal. typhimurium* SL1344. As can be seen in Table 5, only those mice immunized orally with SL3261-pML207 were able to survive an intra-nasal challenge with a dosage of homologous organisms which was otherwise sufficient to kill all immunized animals. Further, the protection conferred by *Sal. typhimurium* SL3261 expressing recombinant M5 protein in M type specific as demonstrated by the inability of intra-nasally challenged mice to tolerate M type 24 Streptococci. The fact that mice were refractory to challenge by intra-nasal innoculation suggested that oral immunization with M5 protein expressing *Sal. typhimurium* SL3261 was sufficient to inpart local immunity.

TABLE 5

Challenge by Intra-Nasal Inoculation of M Type 5 and Type 24 Streptococci or S. typhimurium SL1344 in BALB/c Mice Immunized Orally[1] with Live aro− S. typhimurium Transformed with pMK207 Expressing Type 5 M Protein.

| Challenge Organisms[2] | Dose[3] | Survival[4,5] Unimmunized | Immunized |
|---|---|---|---|
| M5 Streptococci (Smith strain) | $3.9 \times 10^7$ | 0/4 | 6/6 |
| M24 Streptococci (Vaughn strain) | $3.5 \times 10^7$ | 0/4 | 0/6 |
| S. typhimurium (Strain SL1344) | $4.3 \times 10^4$ | 0/4 | 6/6 |

[1]Each immunized mouse received $1.2 \times 10^9$ pMK207 transformed SL3261 S. typhimurium colony forming units (cfu) at day 1 and $1.6 \times 10^9$ cfu at day 5. Each dose was administered orally suspended in 25 µl of phosphate buffered saline (PBS, pH 7.2) containing 5 µg ml$^{-1}$ kanamycin sulfate, and 1 µg ml$^{-1}$ each of paraminobenzoic acid and 2,3-dihydroxybenzoic acid.
[2]Challenge dose was determined as the cfu administered intra-nasally in 20 µl of PBS (10 µl per nostril).
[3]Mice were challenged 13 weeks after the initial immunization (ie. day 1).
[4]Survival was recorded as the number of surviving mice over the number of mice challenged.
[5]Deaths from streptococci occurred between 2 and 4 days, while deaths due to salmonella occurred between 5 and 7 days after challenge. All surviving mice appeared healthy up to 30 days after challenge.

The above examples are not to be construed as limitations, but are merely illustrative of the invention. The invention also encompasses combinations of any number of immunogenic polypeptide sequences of any Streptococcal serotype M protein antigen in a covalent linkage to a natural or synthetic carrier to create a multivalent vaccine broadly protective against serotype M Streptococcus.

The invention also encompasses utilizing an M protein polypeptide sequence as the carrier to which the other sequences are covalently linked, evoking an opsonic response to each one of the Streptococcal serotypes, the polypeptides of which are linked to the carrier, as well as the Streptococcal serotype, the polypeptide of which is serving as the carrier.

The invention also encompasses encoding a nucleotide sequence for such a multivalent polypeptide onto an S. pyogenes chromosome in the region of the M protein structureal gene, cloning it into plasmids and transforming the plasmids into non-virulent host bacterium. Synthetic nucleotide sequences are preferred, but nucleotide sequences obtained from living bacterial cells may also be employed. The invention also encompasses cloning into non-virulent host bacterium already transformed to express immunogenic polypeptides eliciting opsonic responses to type M Streptococcal infections genetic material for the expression of immunogenic polypeptides eliciting opsonic responses to other virulent bacteria species and the covalent linkage of both species polypeptides. The invention also encompasses the resultant attenuated non-virulent host organism, orally administrable as a broad-spectrum vaccine capable of eliciting opsonic responses to more than one species of bacteria.

One skilled in the art would have no difficulty in developing various variations in procedure and products which are within the spirit of the invention and scope of the claims or their equivalent.

We claim:

1. A method for immunizing a mammal against Streptococci infections by eliciting opsonic antibodies to a Streptococcal M protein antigen without eliciting antibodies which are cross-reactive with heart tissue antigens which comprises administering orally to said mammal in an amount effective to confer immunity against Group A Streptococci infection, a therapeutic composition which comprises a biologically acceptable carrier and a non-virulent, live bacterium selected from the group consisting of Salmonella and Streptococcus sanguis, transformed with a plasmid encoding the expressing a serotype-specific entire Streptococcal M protein immunizing antigen compartmentalized intracellularly selected from the serotypes of the group consisting of serotype 5, serotype 6 and serotype 24, releasing the antigen from the bacterium, whereby opsonic antibodies to the antigen of the same serotype as the immunizing antigen elicited, without eliciting antibodies which are cross-reactive with heart tissue antigens, thereby conferring immunity against Streptococci infection to said mammal.

2. A therapeutic composition which comprises in an amount effective to elicit opsonic antibodies and to confer immunity against Group A Streptococci infection in a mammal without eliciting antibodies which are cross-reactive with heart tissue antigens, a biologically acceptable carrier and, a non-virulent, live Salmonella transformed with a plasmid encoding and expressing a serotype-specific entire Streptococcal M protein immunizing antigen compartmentalized intracellularly selected from the group of serotypes 5, 6 and 24 which M protein is normally serologically cross-reactive with human heart tissue antigens, which composition upon oral administration to the mammal elicits opsonic antibodies to the antigen of the same serotype as the immunizing antigen as the antigen is released from the dying bacterium, thereby providing immunity against Streptococci infection to said mammal.

3. A therapeutic composition which comprises a biologically acceptable carrier and in an amount effective to elicit opsonic antibodies to a serotype-specific Streptococcal M protein selected from the group consisting of serotypes 5, 6 and 24, a non-virulent, live transformed bacterium selected from the group consisting of Salmonella and Streptococcus sanguis which contains a plasmid encoding and expressing a serotype-specific entire Streptococcal M protein immunizing antigen compartmentalized intracellularly, which composition upon oral administration to a mammal elicits opsonic antibodies to the antigen of the same serotype as the immunizing antigen, as the antigen is released from the dying bacterium without eliciting antibodies which are cross-reactive with human heart tissue antigens, thereby providing immunity to said mammal against Group A Streptococci infection.

4. A therapeutic composition which comprises a biologically acceptable carrier and in an amount effective to elicit opsonic antibodies to a serotype-specific Streptococcal M protein in a mammal without eliciting antibodies which are cross-reactive with human heart tissue antigens, a non-virulent, live transformed bacterium selected from the group consisting of Salmonella and Streptococcus sanguis expressing a serotype-specific entire Streptococcal M protein immunizing antigen compartmentalized intracellularly, which composition upon oral administration to the mammal elicits opsonic antibodies to the antigen of the same serotype as the immunizing antigen, as the antigen is released from the dying bacterium, thereby providing immunity to said mammal against Group A Streptococci infection.

5. A method for immunizing a mammal against Streptococci infection eliciting opsonic antibodies to a Streptococcal M protein antigen without eliciting antibodies which are cross-reactive with heart tissue antigens, which comprises administering orally to said mammal in an amount effective to confer immunity against Streptococci infection, a therapeutic composition which comprises a biologically acceptable carrier and a non-virulent live, transformed bacterium selected from the group consisting of Salmonella and *Streptococcus sanguis* expressing a serotype-specific entire Streptococcal M protein immunizing antigen compartmentalized intracellularly, releasing the antigen from the dying bacterium, whereby opsonic antibodies to the antigen of the same serotype as the immunizing antigen are elicited, thereby providing immunity to said mammal against Group A Streptococci infection.

6. The therapeutic composition of claim 4 wherein the transformed bacterium is a plasmid-transformed bacterium.

7. The therapeutic composition of claim 6 wherein the bacterium is *Streptococcus sanguis*.

8. The therapeutic composition of claim 6 wherein the bacterium has a mutational variation causing a nutritional deficiency.

9. The therapeutic composition of claim 8 wherein the bacterium is a Salmonella selected from the group consisting of the species *S. paratyphi, S. schottmulleri, S. typhimurium, S. choleraesuis, S. montevideo, S. newport, S. typhi, S. enteritidis, S. gallinarum* and *S. anatum*.

10. The therapeutic composition of claim 9 wherein the Salmonella is *typhymurium*.

11. The therapeutic composition of claim 6 wherein the immunity conferred is systemic.

12. The therapeutic composition of claim 7 wherein the Streptococcus infectious challenge is mucosal.

13. The therapeutic composition of claim 12 wherein the Streptococcus infectious challenge is intranasal.

14. The method of claim 5 wherein the transformed bacterium is a plasmid-transformed bacterium.

15. The method of claim 14 wherein the bacterium is *Streptococcus sanguis*.

16. The method of claim 14 wherein the Salmonella is selected from the group consisting of the species *S. paratyphi, S. schottmulleri, S. typhimurium, S. choleraesuis, S. montevideo, S. newport, S. typhi, S. enteritidis, S. gallinarum* and *S. anatum*.

17. The method of claim 16 wherein the Salmonella is typhymurium.

18. The method of claim 14 wherein the immunity conferred is systemic.

19. The method of claim 15 wherein the Streptococcus infectious challenge is mucosal.

20. The method of claim 19 wherein the Streptococcus infectious challenge is intranasal.

21. The therapeutic composition of claim 3 wherein the bacterium is *Streptococcus sanguis*.

22. The therapeutic composition of claim 3 wherein the bacterium is a Salmonella selected from the group consisting of the species *S. paratyphi, S. schottmulleri, S. typhimurium, S. choleraesuis, S. montevideo, S. newport, S. typhi, S. enteritidis, S. gallinarum* and *S. anatum*.

23. The therapeutic composition of claim 3 wherein the Salmonella has a mutational variation causing a nutritional deficiency.

24. The therapeutic composition of claim 23 wherein the bacterium is *Salmonella typhimurium*.

25. The therapeutic composition of claim 24 wherein the Salmonella is aro—*Sal. typhimurium*.

26. The therapeutic composition of claim 25 wherein the aro—*Sal. typhimurium* is typhimurium SL 3261.

27. The therapeutic composition of claim 3 wherein the serotypes are selected from the group consisting of serotypes 5 and 6.

28. The therapeutic composition of claim 27 wherein the serotype is 5.

29. The therapeutic composition of claim 22 wherein the serotype is 6.

30. The therapeutic composition of claim 3 wherein the serotype is 24.

31. The therapeutic composition of claim 3 wherein the immunity is systemic.

32. The therapeutic composition of claim 21 wherein the Streptococcus infectious challenge is mucosal.

33. The therapeutic composition of claim 32 wherein the Streptococcus infectious challenge is intranasal.

34. The therapeutic composition of claim 3 wherein the M protein is of serotype 5 and the Streptococcus infection of serotype 5.

35. The therapeutic composition of claim 3 wherein the M protein is of serotype 6 and the Streptococcus infection of serotype 6.

36. The therapeutic composition of claim 3 wherein the M protein is of serotype 24 and the Streptococcus infection of serotype 24.

37. The method of claim 1 wherein the bacterium is *Streptococcus sanguis*.

38. The method of claim 1 wherein the Salmonella has a mutational variation causing a nutritional deficiency.

39. The method of claim 38 wherein the Salmonella is selected from the group consisting of the species *S. paratyphi, S. schottmulleri, S. typhimurium, S. choleraesuis, S. montevideo, S. newport, S. typhi, S. enteritidis, S. gallinarum* and *S. anatum*.

40. The method of claim 39 wherein the bacterium is *Salmonella typhimurium*.

41. The method of claim 40 wherein the Salmonella is aro-*Sal. typhimurium*.

42. The method of claim 41 wherein the Salmonella is aro-*Sal. typhimurium* is typhimurium SL 3261.

43. The method of claim 1 wherein the Salmonella multiplies in the mammal to a limited extent then dies releasing the M protein antigen.

44. The method of claim 1 wherein the serotypes are selected from the group consisting of serotypes 5 and 6.

45. The method of claim 44 wherein the serotype is serotype 5.

46. The method of claim 44 wherein the serotype is serotype 6.

47. The method of claim 1 wherein the serotype is serotype 24.

48. The method of claim 1 wherein the immunity is systemic.

49. The method of claim 1 wherein the Streptococci infectious challenge is mucosal.

50. The method of claim 1 wherein the Streptococci infectious challenge is intranasal.

* * * * *